United States Patent [19]

Ito

[11] 4,228,950
[45] Oct. 21, 1980

[54] HORIZONTAL FLOW-THROUGH COIL PLANET CENTRIFUGE

[75] Inventor: Yoichiro Ito, Bethesda, Md.

[73] Assignee: The United States of America as represented by the Department of Health, Education and Welfare, Washington, D.C.

[21] Appl. No.: 966,329

[22] Filed: Dec. 4, 1978

[51] Int. Cl.³ .............................................. B04B 9/08
[52] U.S. Cl. ...................................... 233/25; 210/672
[58] Field of Search ................... 233/25, 26, 27, 23 R, 233/19 R; 210/31 C, 198 C; 128/214 D

[56] References Cited

U.S. PATENT DOCUMENTS

| | | | |
|---|---|---|---|
| 3,994,805 | 11/1976 | Ito | 210/31 C |
| 4,051,025 | 9/1977 | Ito | 210/31 C |
| 4,058,460 | 11/1977 | Ito | 210/31 C |
| 4,146,172 | 3/1979 | Cullis | 233/26 |

*Primary Examiner*—George H. Krizmanich
*Attorney, Agent, or Firm*—Browdy and Neimark

[57] ABSTRACT

A horizontal flow-through coil planet centrifuge wherein flow-through separation columns are rotatably mounted on both sides of a rotor formed by a pair of spaced parallel rotary wings, with suitable intercoupling to avoid the need for rotary seals. Fluid circuit and adjustable valving arrangements are provided for (1) allowing two separations to be simultaneously performed, (2) for connecting the two columns in series to double the partition efficiency, or (3) using one column to separate samples in an ordinary manner while a desired portion of the eluate can be introduced into the second column to recycle.

15 Claims, 8 Drawing Figures

HORIZONTAL FLOW-THROUGH COIL PLANET CENTRIFUGE

FIELD OF THE INVENTION

This invention relates to apparatus for the separation of samples in multiphase solvent systems, and more particularly to apparatus for continuous countercurrent chromatography of the type employing horizontal coiled helical tubular arrays rotating on their longitudinal axes.

BACKGROUND OF THE INVENTION

Various types of horizontal flow-through coil planet centrifuge systems have been previously proposed. A typical previously employed apparatus utilizes a rotating holder or rotor formed by a pair of spaced rotary wings, with a separation column array mounted on one side of the rotor and a counterweight mounted on the other side of the rotor for balancing the apparatus. Suitable drive gearing or other coupling arrangements have been provided for eliminating the necessity of employing rotating seals.

The previously employed centrifuge systems are relatively limited in their operation since they allow only one column holder to be used for separation in a given system and have a relatively limited partition efficiency. Furthermore, in such previous systems with a single column, if recycling of eluate is attempted, the recycling of the early peaks results in contamination of the later peaks.

A preliminary search of the prior art revealed the following prior U.S. patents as showing the present state of the art:
Ito, U.S. Pat. No. 4,051,025
Ito, U.S. Pat. No. 4,058,460

SUMMARY OF THE INVENTION

In the present invention, the apparatus supports a flowthrough separation column on each side of the rotor or holder formed by the rotary wings, and the apparatus is arranged to avoid the use of rotary seals. As above mentioned, in the previous devices only one side of the holder was used for mounting the separation column, while the other side was used for loading a counterweight for balancing the apparatus. The present invention provides the following advantages:

1. Two separations can be simultaneously performed.
2. One column can be a large-scale preparative column and the other can be a small-scale analytical column, so that the apparatus can be used for both preparative and analytical separations.
3. Two columns can be directly connected in series, to double the partition efficiency.
4. A recycling system can be arranged so that one column is used to separate the samples in an ordinary manner while the desired portion of the eluate can be introduced into the second column to recycle. In the previous systems with a single column, the recycling of the early peaks results in contamination of the later peaks. This complication is completely eliminated in the system of the present invention.

Accordingly, a main object of the invention is to overcome the disadvantages and deficiencies of the previously employed horizontal flow-through coil planet centrifuge systems.

A further object of the invention is to provide an improved horizontal flow-through coil planet centrifuge system employing separation columns on both sides of a column-supporting rotor, enabling two separations to be simultaneously carried out, enabling one column to be employed as a large-scale preparative column and the other as a small-scale analytical column so that the apparatus can be used for both preparative and analytical separations, enabling the two columns to be directly connected in series to double the partition efficiency, and enabling one column to be used to separate the samples in an ordinary manner while a desired portion of the eluate can be introduced into the second column to recycle, whereby the recycling of the early peaks does not result in contamination of the later peaks.

A still further object of the invention is to provide an improved horizontal flow-through coil planet centrifuge system employing separation columns on both sides of a column-supporting rotor in a versatile arrangement allowing selected operations, such as the simultaneous use of the two columns independently, each with the same or different solvent systems, separation using the two columns connected in series to obtain doubled partition efficiency, and operation comprising recycling the unresolved peaks by the second column while separating the rest of the peaks in the first column.

A still further object of the invention is to provide an improved versatile horizontal flow-through coil planet centrifuge system employing separation columns on both sides of a column-supporting rotor, not requiring the use of rotating seals, and provided with adjustable-valve arrangements for producing a wide range of fluid circuit configurations to enable the system to perform a corresponding range of important desired functions.

A still further object of the invention is to provide an improved horizontal flow-through coil planet centrifuge system employing separation columns on both sides of a column-supporting rotor, wherein adjustable-valve arrangements are provided for producing a wide range of fluid circuit configurations, which provides highly reproducible results, and which provides a recycling capability which can be automated by programming the operation of its valves.

A still further object of the invention is to provide an improved flow-through coil planet centrifuge system employing separation columns on both sides of a column-supporting rotor, the system having coiled columns with specific capability in performing countercurrent chromatography, such as for large-scale separations, employing large bore columns, or for small-scale analytical separations, employing small-bore columns, and wherein the columns on both sides of the column-supporting rotor can be made identical.

BRIEF DESCRIPTION OF THE DRAWINGS

Further objects and advantages of the invention will become apparent from the following description and claims, and from the accompanying drawings, wherein:

DESCRIPTION OF PREFERRED EMBODIMENTS

Figure 1:
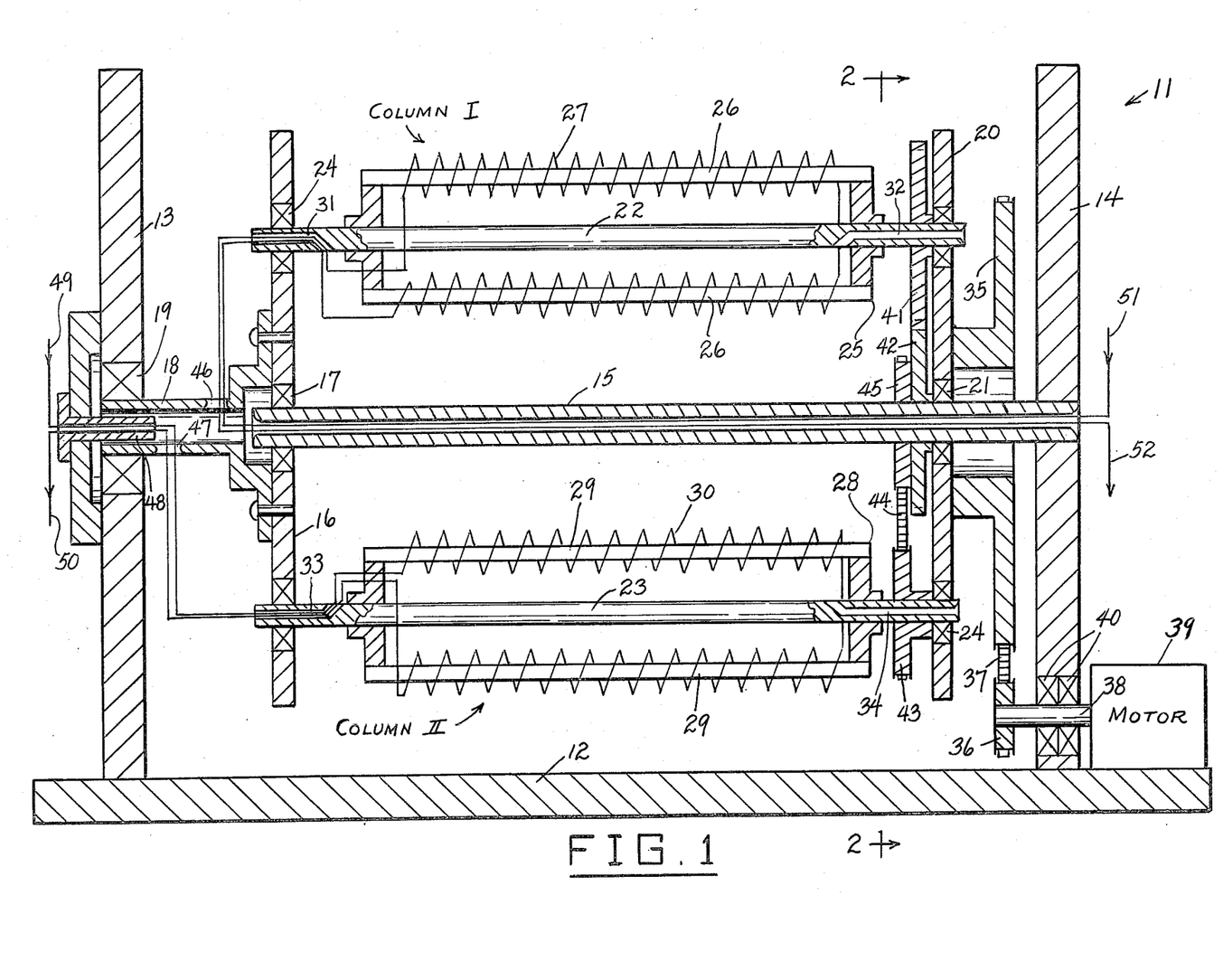
FIG. 1 is a longitudinal vertical cross-sectional view taken through an improved flow-through coil planet centrifuge apparatus according to the present invention.

Referring to the drawings, 11 generally designates a horizontal flow-through coil planet centrifuge apparatus according to the present invention. The apparatus 11 comprises a base plate 12 on which is rigidly secured the opposite parallel vertical upstanding support plates 13 and 14. Rigidly secured to the intermediate portion of support member 14 is a horizontal hollow stationary shaft 15 whose leftward end, as viewed in FIG. 1, is journalled in the intermediate portion of a rotary wing member 16 by means of a conventional bearing assembly 17. A coupling pipe 18 is coaxially rigidly secured to the intermediate portion of rotary wing member 16 and is journalled in the intermediate portion of upstanding support member 13 by means of a conventional bearing assembly 19.

A second rotary wing member 20 is journalled on the stationary horizontal shaft 15 adjacent support member 14 by means of a conventional bearing assembly 21. A pair of horizontal column-supporting shafts 22, 23 are journalled in the rotary wing members 16, 20 by means of conventional bearing assemblies 24 and are located at symmetrically equal radial distances on opposite sides of stationary shaft 15.

Rigidly mounted on shaft 22 is a first column holder 25 including horizontally extending coil-supporting bars 26, 26 carrying a first helically-wound separation coil unit 27. Rigidly mounted on shaft 23 is a second column holder 28 including horizontally extending coil-supporting bars 29, 29 carrying a second helically-wound separation coil unit 30.

Shaft 22 is provided at its opposite ends with respective side and end-opening tube-conveying passages 31, 32 for leading the feed and return ends of coil 27 out of either end of shaft 22, as required. Similarly, shaft 23 is provided at its opposite ends with side and end-opening passages 33, 34 for leading the feed and return ends of coil 30 out of either end of shaft 23, as required.

Coaxially secured on rotary wing member 20 is a large driven gear 35 which is drivingly coupled by a toothed belt 37 to a driving pinion gear 36 mounted on the shaft 38 of an electric motor 39 secured on base 12, said shaft being journalled in upstanding support member 14 by conventional bearing assemblies 40. Secured on shaft 22 adjacent wing member 20 is a planet gear 41 which meshes with an identical stationary gear 42 rigidly secured on hollow shaft 15. Secured on shaft 23 is a gear 43 which is drivingly coupled by a toothed belt 44 to an identical stationary gear 45 rigidly secured on shaft 15 adjacent gear 42.

In the arrangement illustrated in FIG. 1 the feed and return ends of coil 27 are led out through the end passage 31 of shaft 22, extend through an aperture 46 in pipe 18, and extend through hollow shaft 15, emerging at the right end of said shaft 15, as viewed in FIG. 1. The feed and return ends of coil 30 are led out through passage 33 of shaft 23, extend through an aperture 47 in pipe 18, and extend through an axial bushing 48 mounted on vertical support member 13, emerging at the left side of the apparatus, as viewed in FIG. 1. The feed and return tubes of coil 30 are respectively shown at 49 and 50. The feed and return tubes of coil 27 are shown respectively at 51 and 52.

The motor 39 drives the rotary wings 16, 20 around the shaft 15 via gears 36, 35 and belt 37, the rotary wings being linked by the shafts 22, 23. At the same time, the column holders 25, 28 are rotated in a planetary fashion at identical speeds by the shafts 22, 23. The above-described coupling causes column holder 25 to rotate about its own axis at the same angular velocity in the same direction as the rotary wings 16, 20, and causes column holder 28 to rotate around its own axis at the same angular velocity as the rotary wings but in the opposite direction. Thus, the pair of coiled column assemblies 27, 30 mounted on said column holders rotate with respect to the centrifugal force field induced by revolution of the rotary wings 16, 20.

As above mentioned, the flow tubes from the coiled column assembly 27 are passed through the passage 31, the side hole 46 of the coupling pipe 18 and the bore of shaft 15. The flow tubes from the coiled column assembly 30 are similarly passed through the passage 33, the side hole 47 of pipe 18 and finally, the stationary tubular supporting bushing 48 located at the left end of the horizontal central axis of the apparatus. Under this arrangement, these flow tubes are rotated without twisting.

Figure 2:
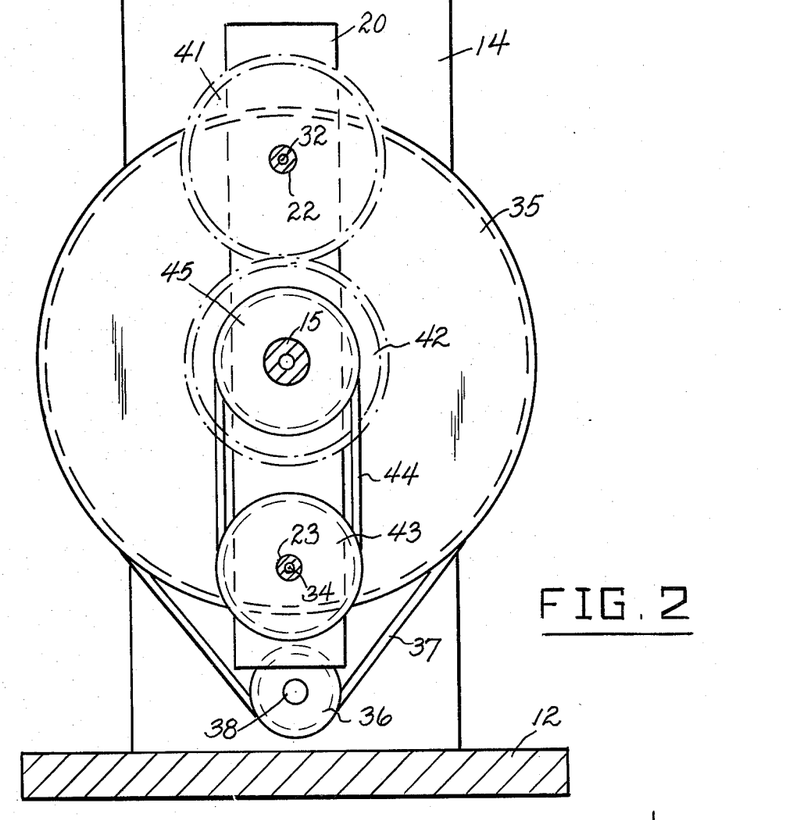
FIG. 2 is a transverse vertical cross-sectional view taken substantially on line 2—2 of FIG. 1.
Figure 5A:
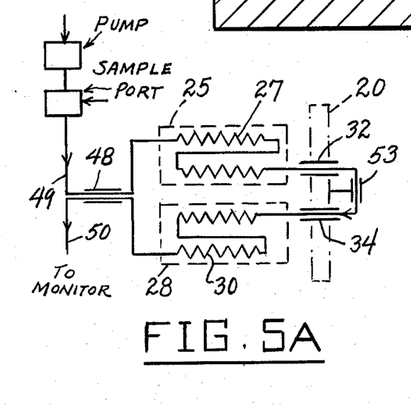
FIGS. 5A and 5B diagrammatically illustrate alternative direct series connections of the separation columns.
Figure 5B:
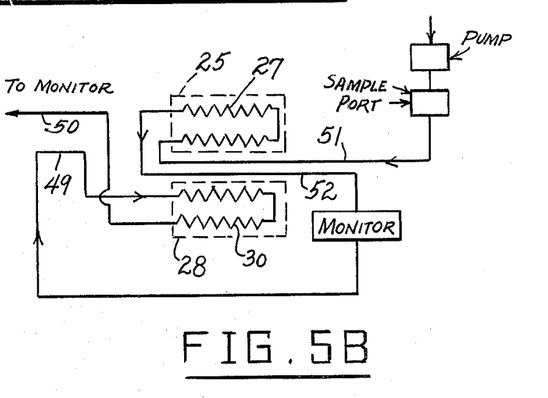

Although the two column assemblies 27 and 30 may be used independently for separation, as in the arrangement of FIGS. 1 and 2, they can also be connected in series to double the partition efficiency. This may be done in two ways: (1) the flow tubes from each column may be connected directly on the rotary wing 20 after passing through the passages 32, 34 of the respective shafts, as shown diagrammatically in FIG. 5A. The portion of the flow tube outside the rotary wing 20 may be supported by a tube guide 53 eccentrically located on and secured to said wing so as to clear the toothed pulley 35. Since the columns 25, 28 rotate in opposite directions, the flow tubes 49, 50 are free from twisting. (2) The connections of the two coiled column assemblies may also be made externally, as shown diagrammatically in FIG. 5B, with a slight excess of dead space in the flow tube. This alternative arrangement facilitates the monitoring of the separation before the eluate enters the second column, thus having an advantage over the arrangement of FIG. 5A.

In operation, each column is first filled with one phase (stationary phase) of an equilibrated two-phase solvent system and the sample solution (in either the stationary or mobile phase) is injected through the sample port, located between the pump and the separation column. Then the other phase (mobile phase) is pump through the flow tube into the column while the apparatus is rotated at a desired revolutional speed. The eluate is monitored, through a suitable detector, and fractionated, as in the conventional chromatographic systems.

Figures 3, 4:
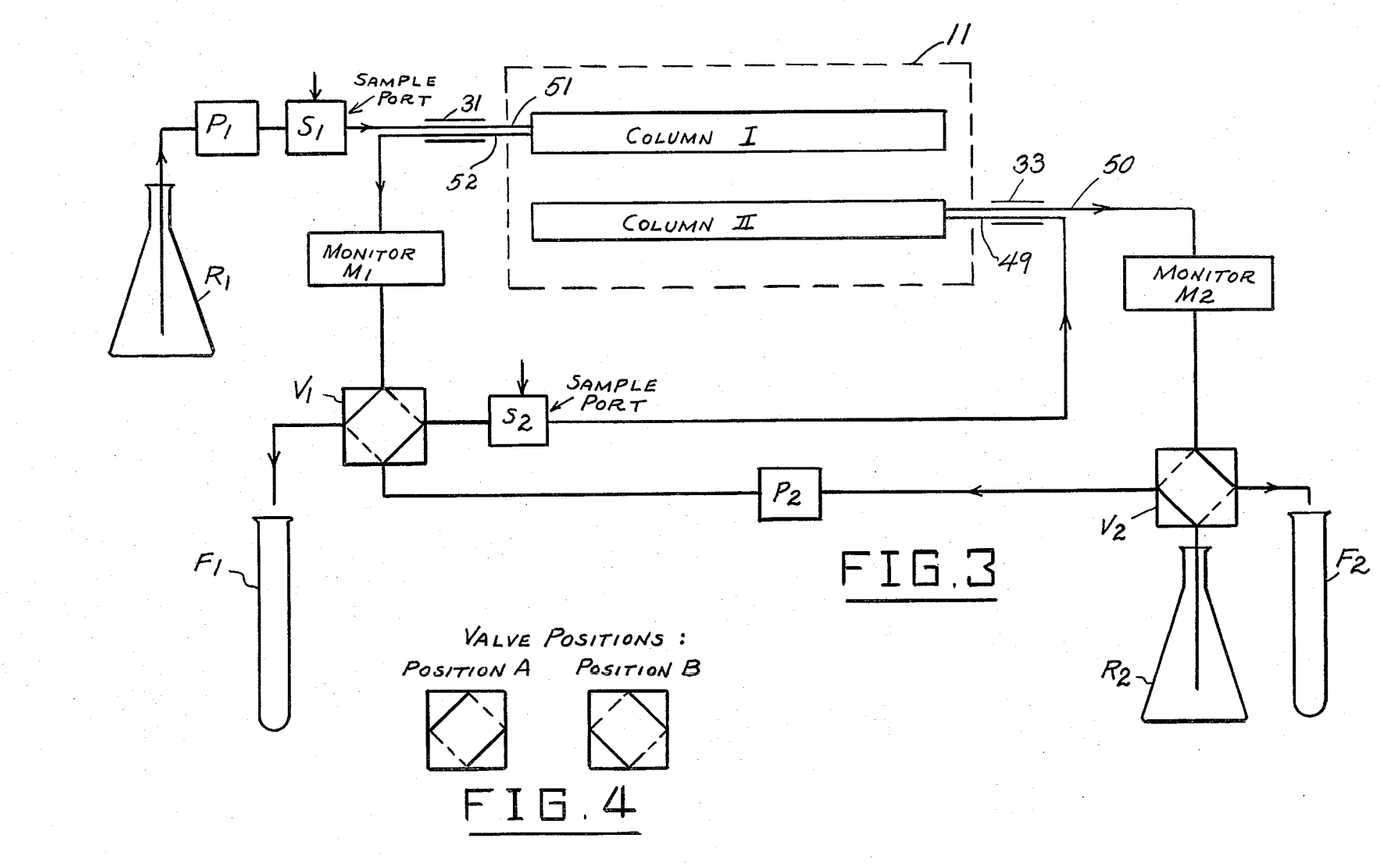
FIG. 3 is a schematic view of a universal elution system according to the present invention, employing the apparatus of FIG. 1.
FIG. 4 is an explanatory view showing diagrammatically the two different positions of the 4-way valves employed in the system of FIG. 3.

FIG. 3 diagrammatically illustrates an example of a universal elution system employing an apparatus similar to that of FIGS. 1 and 2, in accordance with the present invention. The system of FIG. 3 includes a pair of reservoirs $R_1$ and $R_2$, pumps $P_1$ and $P_2$, flow-through monitors $M_1$ and $M_2$, 4-way valves $V_1$ and $V_2$, and fraction collectors $F_1$ and $F_2$, connected in a fluid circuit with apparatus 11, as illustrated. Column I represents the rotary column assembly including the coiled column assembly 27 and Column II represents the rotary column assembly including the coiled column assembly 30. The elution system of FIG. 3 allows versatile operation, such as (1) simultaneous use of the two columns independently, each with the same or different solvent systems, (2) separation using the two column assemblies connected in series to obtain doubled partition efficiency, and (3) recycling the unresolved peaks by the second column (Column II) while separating the rest of the peaks in the first column (Column I), as follows:

1. Simultaneous Operation Using Two Columns Independently

Valve $V_1$ is set at "Position A" and valve $V_2$ is set at "Position B", as shown in FIG. 3. Pump $P_1$ introduces the mobile phase from reservoir $R_1$ to elute through Column I, the eluate being monitored by monitor $M_1$ and then collected into fraction collector $F_1$ via valve $V_1$. Similarly, pump $P_2$ introduces the mobile phase from reservoir $R_2$ into Column II via valves $V_2$ and $V_1$, the eluate from Column II being monitored by monitor $M_2$ and fractionated into collector $F_2$ via valve $V_2$. Since these two channels are completely separated, different two-phase solvent systems can be used for the respective channels.

2. Connection of the Two Columns in Series

For this purpose both valves $V_1$ and $V_2$ are set at "Position B" and pump $P_2$ is deenergized. With this arrangement, pump $P_1$ pumps the mobile phase from reservoir $R_1$ into Column I. The eluate exiting from Column I is monitored by monitor $M_1$ and then goes into Column II via valve $V_1$. The eluate from Column II is again monitored, by monitor $M_2$, and is fractionated into collector $F_2$.

3. Recycling Operation

For recycling unresolved peaks, the positions of the valves $V_1$ and $V_2$ are changed during the operation, as follows:

(a) Elution is first performed through Column I with valve $V_1$ at "Position A", valve $V_2$ at "Position B" and pump $P_2$ deenergized. The pump $P_1$ introduces the mobile phase into Column I to elute the sample injected at the sample port $S_1$. The eluate is monitored by monitor $M_1$ and is fractionated into collector $F_1$ via valve $V_1$, at "Position A", before the unresolved peak aimed for recycling is detected by monitor $M_1$.

(b) When the aimed-for peak is eluted through Column I (detected by monitor $M_1$), valve $V_1$ is shifted to "Position B", which then introduces the eluate of Column I into Column II.

(c) When monitor $M_1$ shows the end of the unresolved peak, valve $V_1$ is shifted to "Position A", to isolate the unresolved peak in Column II from the rest of the peaks still uneluted through Column I. Pump $P_2$ is now energized, to pump the same mobile phase in reservoir $R_2$ through Column II to elute the isolated unresolved peak. This operation also resumes the fractionation of the rest of the eluate from Column I into collector $F_1$.

(d) When monitor $M_2$ detects the elution of the peak through Column II, valve $V_2$ is shifted to "Position A", to recycle the peak or peaks via pump $P_2$ and valve $V_1$, at "Position A", back into Column II. Recycling is continued until the peaks are well resolved.

(e) When the peaks are well resolved, valve $V_2$ is shifted to "Position B", to elute the peaks into fraction collector $F_2$.

For the above-described recycling operation, it is desirable to perform a preliminary separation of the solutes to predetermine accurately the elution time of the unresolved peak. Because of the high reproducibility of the above-described procedure, the recycling operation can be automated by suitably programming the operation of the valves.

If the original sample is known to be entirely composed of two or more solutes with similar partition coefficients, the above-described operation 2 (two columns connected in series) is performed. When this operation still fails to resolve the peaks, recycling operation can be performed by simply shifting valve $V_1$ to "Position A" and valve $V_2$ to "Position A", and employing pump $P_2$ to recycle the peaks through Column II. In this case, operation for isolating the unresolved peaks is not required.

Figure 6:
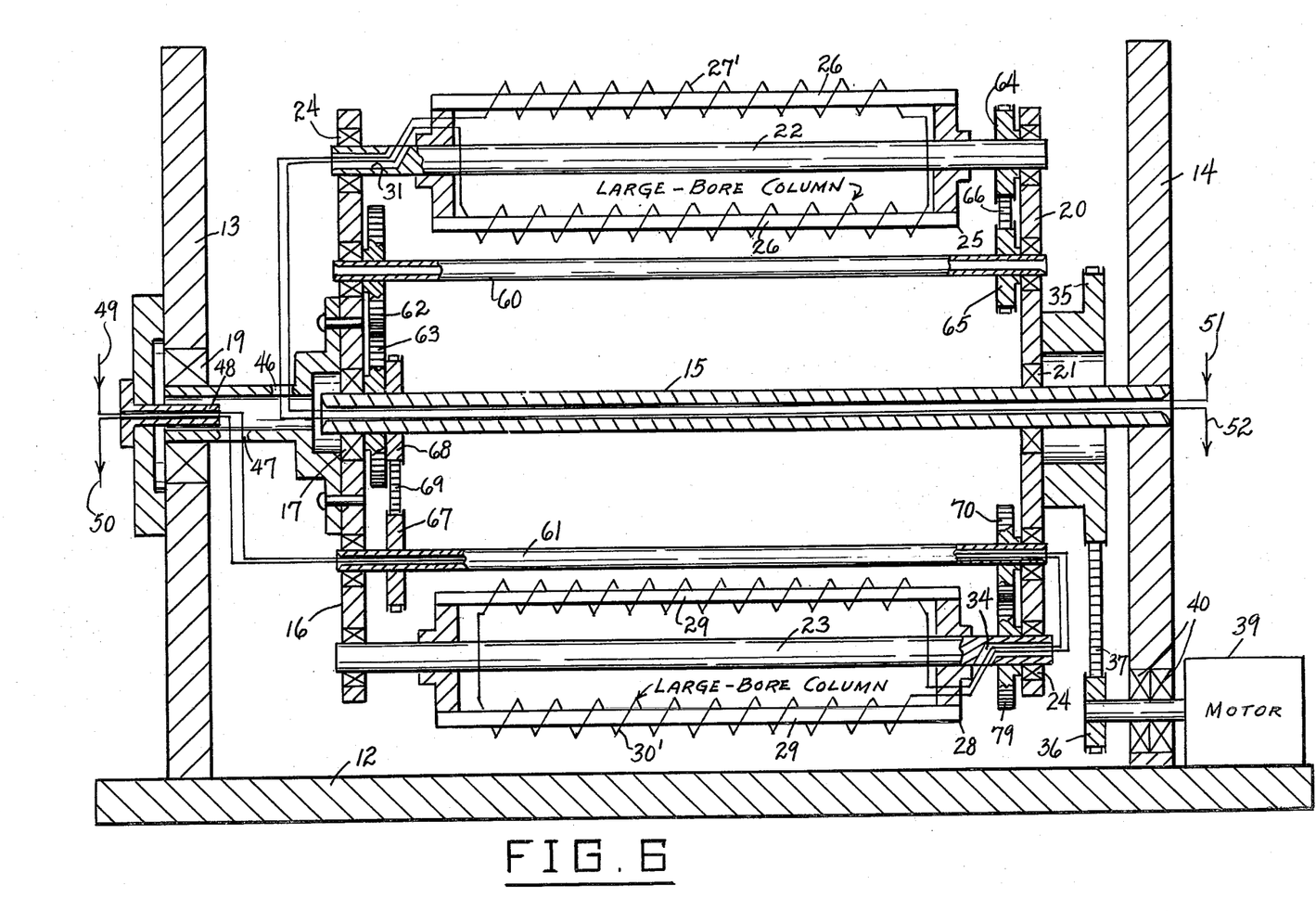
FIG. 6 is a longitudinal vertical cross-sectional view similar to FIG. 1, showing a modification, for employing identical large bore columns on both sides of the column-supporting rotor, for performing large-scale separations.

A series of experiments with the apparatus of FIG. 1 has shown that the two coiled columns 27 and 30 each has specific capability in performing countercurrent chromatography. The gear-driven column 27 permits stable retention of the stationary phase for a variety of two-phase solvent systems when column 27 is of the large-bore type, and therefore is particularly suitable for large-scale preparative separations. The pulley-driven column 30, when of the small-bore type, provides efficient mixing of the two phases and is suitable for small-scale analytical separations. With minor modifications of the apparatus of FIG. 1, both columns can be made identical, namely, either of the large-bore or small-bore type. FIG. 6 shows an example of an apparatus equipped with large-bore type columns 27' and 30' on both sides of shaft 15. A pair of rotary hollow shafts 60, 61, journalled symmetrically on opposite sides of the stationary shaft 15 in wing members 16, 20 are provided to produce the desired motion of the columns, and the lower hollow shaft 61 is employed to support the flow tubes 49, 50 for the lower column 30'. As shown in FIG. 6, shaft 60 has a gear 62 which meshes with a stationary identical gear 63 on shaft 15, and column holder shaft 22 has a toothed pulley 64 driven by an identical toothed pulley 65 on shaft 60 by means of a toothed drive belt 66. Shaft 61 has a toothed pulley 67 drivingly coupled to a stationary identical toothed pulley 68 on fixed shaft 15 by means of a toothed drive belt 69. Column holder shaft 23 has a gear 79 meshing with an identical gear 70 on shaft 61. The flow tubes 49, 50 extend through tubular member 48, shaft 61 and the passage 34 at the right end of column shaft 23, as viewed in FIG. 6.

Figure 7:
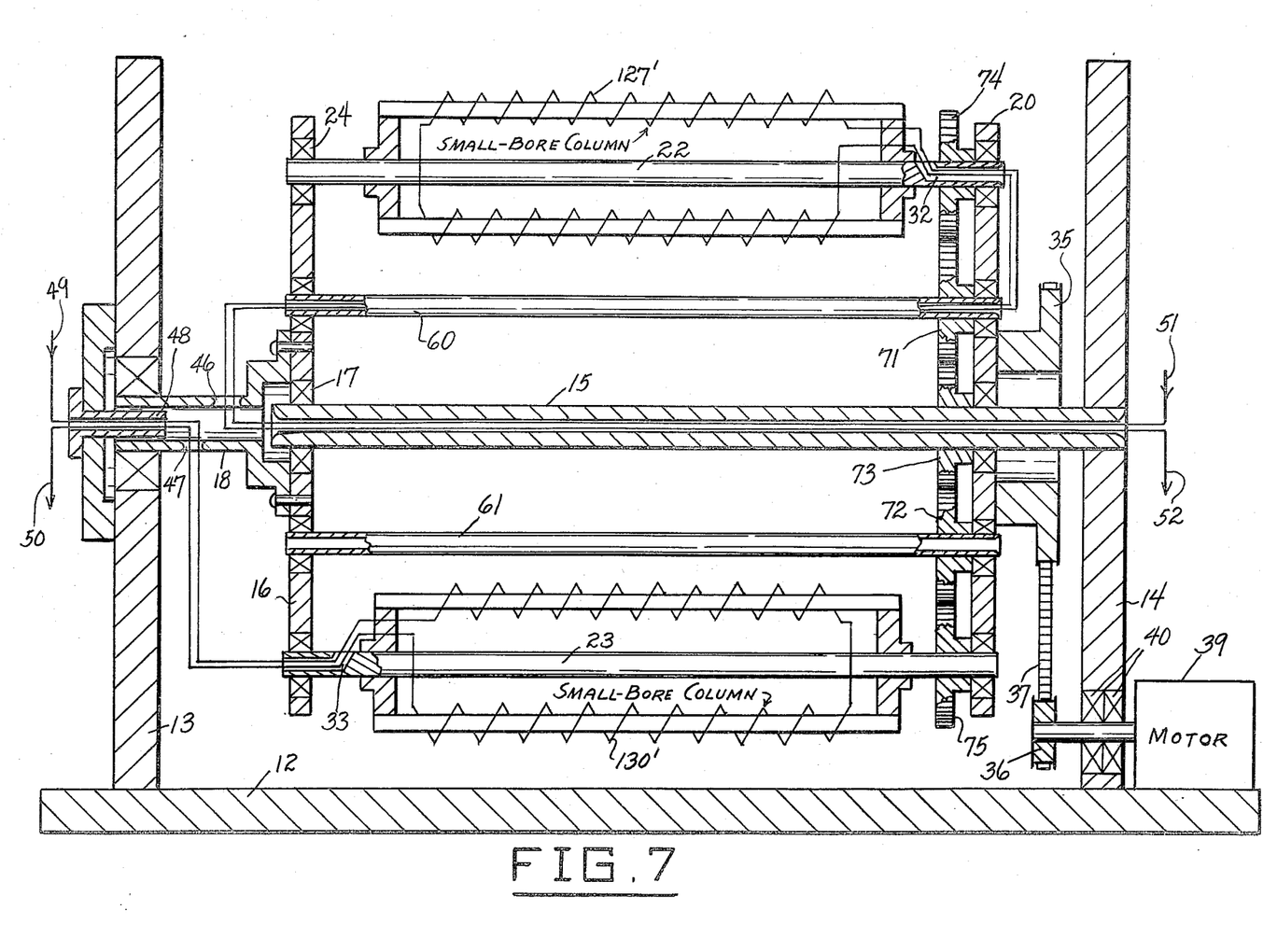
FIG. 7 is a longitudinal vertical cross-sectional view similar to FIG. 1, showing another modification, for employing identical small-bore columns on both sides of the column-supporting rotor, for performing small-scale analytical separations.

FIG. 7 shows a similar apparatus equipped with small-bore type columns 127' and 130' on both sides of shaft 15, and with rotary hollow shafts 60, 61 similar to FIG. 6, symmetrically journalled in wing members 16, 20 at opposite sides of shaft 15. Shafts 60 and 61 have identical gears 71,72 meshing with an identical stationary gear 73 on shaft 15. Shafts 22, 23 have gears 74, 75 identical to and meshing with the respective gears 71,72. The flow tubes 51, 52 from column 127' extend through hollow shafts 60 and 15 via end passage 32 of shaft 22. The flow tubes 49, 50 of column 130' extend through tubular member 48 via the left end passage 33 of shaft 23, as in FIG. 1.

The flow tubes 49–52, like the inlet and outlet conduits of the centrifuge described in the above-mentioned U.S. Pat. No. 4,058,460 of Ito, are of the flexible type with slack to allow them to flex freely during planetary movements of the column assemblies.

While certain specific embodiments of an improved horizontal flow-through coil planet centrifuge apparatus have been disclosed in the foregoing description, it will be understood that various modifications within the scope of the invention may occur to those skilled in the art. Therefore it is intended that adaptations and modifications should and are intended to be comprehended within the meaning and range of equivalents of the disclosed embodiments.

What is claimed is:

1. A horizontal flow-through coil planet centrifuge apparatus comprising a support, a stationary shaft member horizontally rigidly mounted in said support, a pair of spaced parallel wing members, means rotatably supporting said wing members on said shaft member perpendicularly thereto, respective horizontal separation column assemblies journalled respectively for independent, planetary motions between portions of said wing members located on opposite sides of said shaft member, respective inlet and outlet flow tubes connected to each of said column assemblies to define flow paths therethrough, and means to simultaneously rotate said column assemblies around their rotational axes relative to said wing members and to revolve said wing members around said shaft member at relative rates and directions to avoid twisting of the flow tubes.

2. The flow-through centrifuge apparatus of claim 1, and wherein said stationary shaft member is hollow and wherein the flow tubes of one of the column assemblies extend through said hollow stationary shaft member.

3. The flow-through centrifuge apparatus of claim 2, and stationary flow tube guide means on the support axially aligned with and spaced from the stationary shaft member, the flow tubes of the other column assembly extending through said stationary flow tube guide means.

4. The flow-through centrifuge apparatus of claim 1, and wherein the means to simultaneously rotate and revolve said column assemblies includes respective intermediate shafts journalled in the wing members on opposite sides of said stationary shaft member, planet gear means drivingly coupling said intermediate shafts to said stationary shaft member so as to rotate the intermediate shafts responsive to the revolution of the wing members, and means gearingly coupling said intermediate shafts to the respective column assemblies.

5. The flow-through centrifuge apparatus of claim 4, and wherein said intermediate shafts are tubular and are adapted to supportingly receive the flow tubes.

6. The flow-through centrifuge apparatus of claim 4, and wherein the column assemblies on the opposite sides of said stationary shaft member have columns with the same order of bore size.

7. A horizontal flow-through centrifuge apparatus of the coil planet type comprising a support, a shaft member horizontally rigidly mounted on said support, a pair of spaced parallel wing members, means rotatably supporting said wing members on said shaft member perpendicularly thereto, respective horizontal separation in column assemblies journalled respectively for independent, planetary motions between portions of said wing members located on opposite sides of said shaft member, respective inlet and outlet flow tubes connected to each of said column assemblies to define flow paths therethrough, means to simultaneously rotate said column assemblies around their rotational axes relative to said wing members and to revolve said wing members around said shaft members, and fluid circuit means connected to said flow tubes and including changeable means to selectively provide at least two different fluid circuit configurations containing the separation column assemblies.

8. A horizontal flow-through centrifuge apparatus of the coil planet type comprising a support, a shaft member horizontally rigidly mounted on said support, a pair of spaced parallel wing members, means rotatably supporting said wing members on said shaft member perpendicularly thereto, respective horizontal separation column assemblies journalled between portions of said wing members located on opposite sides of said shaft member, respective inlet and outlet flow tubes connected to each of said column assemblies to define flow paths therethrough, means to simultaneously rotate said column assemblies around their rotational axes relative to said wing members and to revolve said wing members around said shaft member, and fluid circuit means connected to said flow tubes and including changeable means to selectively provide at least two different fluid circuit configurations containing the separation column assemblies, and wherein said changeable means comprises respective multi-position valves connected with said column assemblies.

9. The centrifuge apparatus of claim 7, and wherein said changeable means comprises respective multi-position valves connected to the outlet flow tubes of the column assemblies and means to at times connect the column assemblies together through said valves.

10. The centrifuge apparatus of claim 9, and respective flow-monitoring means connected between said outlet flow tubes and the multi-position valves.

11. The centrifuge apparatus of claim 9, and respective sample injection means connected to said inlet flow tubes.

12. A horizontal flow-through centrifuge apparatus of the coil planet type comprising a support, a shaft member horizontally rigidly mounted on said support, a pair of spaced parallel wing members, means rotatably supporting said wing members on said shaft member perpendicularly thereto, respective horizontal separation column assemblies journalled between portions of said wing members located on opposite sides of said shaft member, respective inlet and oultet flow tubes connected to each of said column assemblies to define flow paths therethrough, means to simultaneously rotate said column assemblies around their rotational axes relative to said wing members and to revolve said wing members around said shaft member, and fluid circuit means connected to said flow tubes and including changeable means to selectively provide at least two different fluid circuit configurations containing the separation column assemblies, and wherein one of said fluid circuit configurations includes means to enable said separation column assemblies to operate independently of each other and the other fluid circuit configuration includes means to connect said separation column assemblies in series.

13. The centrifuge apparatus of claim 12, and wherein said fluid circuit means includes respective sample injection means connected to said inlet flow tubes.

14. The centrifuge apparatus of claim 12, and wherein said changeable means comprises respective 2-position, 4-way valves interconnecting the two separation column assemblies so that the separation column assemblies can be operated independently of each other in one mode of valve position settings and are connected in series in another mode of valve position settings.

15. The centrifuge apparatus of claim 14, and conduit means interconnecting the valves with the separation column assemblies so that in said one mode of valve position settings one separation column assembly can be used to separate samples in an ordinary manner, and in said another mode of valve position settings a desired portion of the eluate from said one separation column assembly can be introduced into the other separation column assembly to recycle.

* * * * *